United States Patent [19]
Belfer et al.

[11] Patent Number: 6,106,854
[45] Date of Patent: Aug. 22, 2000

[54] DISINFECTANT COMPOSITION FOR INFECTIOUS WATER AND SURFACE CONTAMINATIONS

[76] Inventors: William A. Belfer, 804 W. Park Ave.; Phillip J. Petillo, 1206 Herbert Ave., both of Ocean Township, N.J. 07712

[21] Appl. No.: 09/047,570

[22] Filed: Mar. 25, 1998

[51] Int. Cl.[7] .................................................. A01N 25/02
[52] U.S. Cl. ........................... 424/405; 424/406; 424/45; 424/76.8; 424/613; 424/616; 424/641; 424/653; 424/702; 424/717; 424/722
[58] Field of Search ..................... 570/384, 417; 424/45, 667–673, 53, 46, 76.3, 76.5–76.9, 405, 406, 57, 55–58, 657–660, 613, 614, 616, 641, 643, 653, 702, 717, 722

[56] References Cited

U.S. PATENT DOCUMENTS

| | | | |
|---|---|---|---|
| Re. 16,593 | 4/1927 | Freng et al. | 424/53 |
| 93,607 | 8/1869 | Fish | 424/76.6 |
| 124,251 | 3/1872 | Lauer | 424/642 |
| 153,707 | 8/1874 | Devlan | 510/417 |
| 864,219 | 8/1907 | Worner | 424/667 |
| 984,106 | 2/1911 | Reed et al. | 426/667 |
| 1,584,173 | 5/1926 | Holzapfel | 434/642 |
| 3,317,372 | 5/1967 | Hart | 424/76.21 |
| 4,719,111 | 1/1988 | Wilson | 424/195.1 |
| 4,738,840 | 4/1988 | Simon et al. | 424/51 |
| 5,574,017 | 11/1996 | Guntheil | 514/19 |
| 5,648,064 | 7/1997 | Gaffar et al. | 424/53 |
| 5,753,217 | 5/1998 | Christopfel | 424/76.9 |

FOREIGN PATENT DOCUMENTS

| | | |
|---|---|---|
| 307376 | 3/1989 | European Pat. Off. . |
| 7000210 | 8/1970 | South Africa . |

*Primary Examiner*—Neil S. Levy
*Attorney, Agent, or Firm*—Ezra Sutton

[57] ABSTRACT

An asepsis disinfectant composition in liquid form having germicidal and biofilm cleansing properties comprising an anti-infective, an antiseptic agent, and an anti-biofilm agent for killing pathogenic and non-pathogenic organisms being in the range of 13.0% to 45.5% by weight of the disinfectant composition; a water purifying agent for acting as a detergent, a sanitizer and a bactericide being in the range of 4.0% to 14.0% by weight of the disinfectant composition; a cleansing agent for acting as an astringent and an abradant in the removal of biofilm from contaminated surfaces, and as a bactericide and fungicide being in the range of 10.0% to 23.0% by weight of the disinfectant composition; an anti-oxidant and stabilizer agent for stabilizing anti-infective and antiseptic agent in the liquid disinfectant composition being in the range of 4.0% to 8.0% by weight of the disinfectant composition; a scrubbing agent for acting as an abrasive and a cleanser for the removal of biofilm from contaminated surfaces being in the range of 4.0% to 8.0% by weight of the disinfectant composition; at least one pH adjuster for acidifying disinfectant composition from a basic or neutral condition to a slightly acidic condition having a pH in the range of 5.0 to 6.9 being in the range of trace amounts to 2.0% by weight of the disinfectant composition; and a diluent for diluting and dissolving into solution the anti-oxidant and stabilizer agent, the scrubbing agent, and the pH adjuster and control agent; the diluent being in the range of 35.0% to 50.0% by weight of the disinfectant composition.

35 Claims, 2 Drawing Sheets

BACTERIAL RATE OF DESTRUCTION CURVE

DISINFECTANT COMPOSITION FOR INFECTIOUS WATER AND SURFACE CONTAMINATIONS

FIELD OF THE INVENTION

The invention relates to an improved medical and dental disinfectant composition which, when applied to contaminated surfaces and to infectious air, water and vacuum lines, will destroy or inactivate viruses, bacteria, funguses, and parasites on contact. More particularly, this invention relates to a disinfectant composition which cleans and decontaminates water systems and water lines; medical and dental devices; metal, ceramic, plastic and wood surfaces; furniture; floors and walls; and the like; and which fulfills the guidelines for disinfectant ingredients established by the Food and Drug Administration, as listed in the Federal Register: Volume 43, Number 166. This composition is cost effective, easy to use, environmentally safe, non-toxic (physiologically safe) to humans, and greatly reduces pathogens on contact.

BACKGROUND OF THE INVENTION

The American Dental Association Council on Scientific Affairs recommended in December 1995 that industry and the research community undertake an aggressive and ambitious product development program to improve the water quality from dental units. It declared that by the year 2000, water delivered to patients during non-surgical dental procedures should consistently contain no more than 200 colony forming units per milliliter of aerobic mesophilic heterotrophic bacteria at any point in time in the unfiltered output of the dental unit. The impetus for the ADA statement was the concern in the scientific community about the rising incidence of infectious disease among patient populations, the high incidence of immuno-compromised patients that dentists were treating, and the realization that water coming from dental units is less than the standard for potable drinking water. The potential for cross-contamination existed and there was fear that patients were being subjected to risk during routine dental procedures. Research showed that there were two causes of bacterial contamination in the dental water lines. The first was the persistence of biofilm, a build-up of bacterial colonies (plaque) which adhered to walls of the tubing. The other was back-flow of bacterial laden fluids from the dental handpieces and water syringes, a result of reversal pressures or diffusion or backgrowth of the bacterial contaminants. It has been long known that *Legionella pneumophila*, the infective agent of Legionnaire's disease, was prevalent in contaminated water supplies. However, a most alarming report was that dental professionals had a significant occupational exposure to Legionella from aerosolization of dental unit water. This was confirmed by the high levels of anti-Legionella antibodies found in their blood. A mild, self-limiting form of Legionella disease, Pontiac fever, was the most common illness, and in one case there is a report of a dentist who died after contracting Legionella pneumonia from his own contaminated dental waterlines. Based on these facts, the implications for public health concerns are very serious to both practitioner and patient.

To date there have been few viable solutions to this problem. Biofilm is resistant to removal and the agents that have been used are either caustic, corrosive, toxic or damaging to patients, staff personnel, equipment or the environment. The remedies that are available are either not completely effective or they damage dental devices, dental components and parts, and/or dental water units.

Aside from the ADA there are regulatory agencies that are involved in this issue. The Occupational Safety and Health Agency (OSHA) has proposed regulations which require the elimination of hazardous bio-aerosols in the workplace, including dental offices; and because of the prevalence of Legionella in dental water lines, OSHA and public pressure will cause a strong demand for a solution to the problem. Moreover, as media focus becomes more acute, public awareness will stimulate the dental profession to introduce new systems and protocols for waterline decontamination.

There remains a need for an improved asepsis disinfectant composition in solution form for cleansing and decontaminating of soiled and contaminated surfaces, as well as infectious air, water and vacuum lines of dental and medical equipment in order to kill and/or inactivate viruses, bacteria, funguses, and parasites on contact with the disinfectant solution. Additionally, the disinfectant composition should be non-harmful (non-toxic and non-irritating) to humans, environmentally safe, non-binding to medical and dental equipment, and non-corrosive and non-absorptive (will not stain) to metals, plastics, ceramics, woods and material fabrics.

DESCRIPTION OF THE PRIOR ART

Antiseptic, germicidal, and disinfectant compositions having various formulations have been disclosed in the prior art. For example, U.S. Pat. No. 5,709,546 discloses a bactericide solution for sanitizing dental equipment. This liquid bactericidal agent of the prior art does not disclose the formulation of the disinfectant composition of the present invention.

U.S. Pat. Nos. 5,648,075; 5,578,664; 5,071,648; 4,031,209; and 3,911,107 all disclose iodine based germicidal and antiseptic compositions having various iodine complexes therein. These antiseptic compositions of these prior art patents do not disclose the formulation of the disinfectant composition of the present invention.

U.S. Pat. No. 5,308,611 discloses an antiseptic composition including a biocidal agent and at least one nonionic surfactant. This liquid antiseptic composition of the prior art does not disclose the formulation of the disinfectant composition of the present invention.

None of the prior art patents teach or disclose the ingredient composition of the disinfectant composition of the present invention that includes a germicidal, anti-infective and antiseptic agent, a water purifying agent, a cleansing agent, an anti-oxidant and stabilizer agent, a scrubbing agent, a pH adjuster and control agent, a gas propellant and a diluent in which the composition is non-toxic to humans, environmentally safe and kills pathogenic bacteria on contact.

Accordingly, it is an object of the present invention to provide a disinfectant composition in solution form for cleansing and decontaminating of contaminated and soiled surfaces, and infectious air, water and vacuum lines in order to kill and/or inactivate viruses, bacteria, funguses, and parasites on contact.

Another object of the present invention is to provide a disinfectant composition which disinfects, filters, scrubs, cleans and decontaminates water systems having air and water lines; medical and dental devices; air filters; surfaces made of metal, plastic and wood; furniture; floors; walls; tile grout and the like.

Another object of the present invention is to provide a disinfectant composition comprising hydrogen peroxide, an iodine halide complex, boric acid, lecithin, and zinc oxide such that these compounds are readily soluble in water or alcohol, stable, and have germicidal and cleansing properties.

Another object of the present invention is to provide a disinfectant composition that is non-harmful to humans, safe and non-irritating to the skin, lungs, eyes and mucous membranes and having no caustic or inhalation problems to humans; and can be used as a skin disinfectant for humans and animals. In addition, the disinfectant is safe, non-toxic, and non-binding to the dental components that the disinfectant comes in contact with, such that patients will not be bothered by residual chemical tastes.

Another object of the present invention is to provide a disinfectant composition that is non-corrosive to medical grade metals that include aluminum, brass, and stainless steel; and is also non-absorptive into materials that include fabrics (will not stain), plastics, ceramics, and woods.

Another object of the present invention is to provide a disinfectant composition that can be used as a soak (i.e. as in surface wipe mini-towels), as a flush in washing and rinsing of medical devices, or as an aerosol spray to disinfect and clean inner and outer surfaces of biofilm and microbial contaminants within air, water and vacuum systems and their respective air, water and vacuum lines.

Another object of the present invention is to provide a disinfectant composition that is environmentally safe wherein all of the ingredients of the composition that are introduced into a waste sewerage system are naturally occurring, non-toxic, non-flammable, non-accumulative and are biodegradable by organisms within the sewerage treatment cycle.

A further object of the present invention is to provide a disinfectant composition that may be mass produced at a low material coat for ingredients in an automated and economical manner and being readily affordable by the practitioner.

SUMMARY OF THE INVENTION

In accordance with the present invention, there is provided an asepsis disinfectant composition in liquid form having germicidal and biofilm cleansing properties including an anti-infective, germicidal and antiseptic agent for killing pathogenic and non-pathogenic organisms selected from the group consisting of hydrogen peroxide, urea hydrogen peroxide and betaine hydrochloride, being in the range of 13.0% to 45.5% by weight of the disinfectant composition; a water purifying agent for acting as a detergent, a sanitizer and a bactericide selected from the group consisting of iodine, iodine penta-fluoride, iodine monobromide, iodine chloride, iodine-halides, iodophors and tetraglycine hydroperiodide, being in the range of 4.0% to 14.0% by weight of the disinfectant composition; a cleansing agent for acting as an astringent and an abradant in the removal of biofilm from contaminated surfaces, and as a bactericide and fungicide selected from the group consisting of boric acid, meta boric acid, salts of boric acid, benzoic acid, bismuth with halogen, bismuth subnitrate, chlorhexidine, chlorhexidine gluconate, citric acid, hippuric acid, hydrochloric acid, kojic acid, lauric acid, sodium oleate, sodium potassium bicarbonate alkalizer and zinc sulfate; being in the range of 10.0% to 23.0% by weight of the disinfectant composition; an anti-oxidant and stabilizer agent for stabilizing the anti-infective and antiseptic agent in the liquid disinfectant composition selected from the group consisting of lecithin, glycerides, choline, linoleic acid, linoleic diethanolamide and black walnut hull tincture (10%) being in the range of 4.0% to 8.0% by weight of the disinfectant composition; a scrubbing agent for acting as an abrasive and a cleanser for the removal of biofilm from contaminated surfaces selected from the group consisting of zinc oxide, borax, calcium bicarbonate, calcium hydroxide, magnesium hydroxide, magnesium oxide, potassium carbonate, potassium oxide, selenium oxide and sodium bicarbonate being in the range of 4.0% to 8.0% by weight of the disinfectant composition; at least one pH adjuster for acidifying the disinfectant composition from a basic or neutral condition to a slightly acidic condition having a pH in the range of 5.0 to 6.9; the pH adjuster and control agent is selected from the group consisting of sodium hydroxide, sodium bicarbonate, acetic acid, ascorbic acid, benzoic acid, citric acid, fumaric acid, glycine, hippuric acid, hydrochloric acid, hydroiodic acid, kojic acid, nitric acid, phosphoric acid, sulfuric acid and ethanolamine; being in the range of trace amounts to 2.0% by weight of the disinfectant composition; and a diluent for diluting and dissolving into solution the anti-oxidant and stabilizer agent, the scrubbing agent, and the pH adjuster and control agent; the diluent selected from the group consisting of water, ethanol, 2-isopropanol and polyvinyl alcohol being in the range of 35.0% to 50.0% by weight of the disinfectant composition.

The asepsis disinfectant composition of the present invention may further include a gas propellant for acting as a gaseous carrier in order to provide a pressurized aerosol spray selected from the group consisting of compressed air, carbon dioxide, helium and nitrogen being in the range of 2.0% to 4.0% by weight of the disinfectant composition.

BRIEF DESCRIPTION OF THE DRAWINGS

Further objects, features, and advantages of the present invention will become apparent upon consideration of the detailed description of the presently-preferred embodiments, when taken in conjunction with the accompanying drawings wherein.

DETAILED DESCRIPTION OF THE PREFERRED EMBODIMENT

Figure 1:
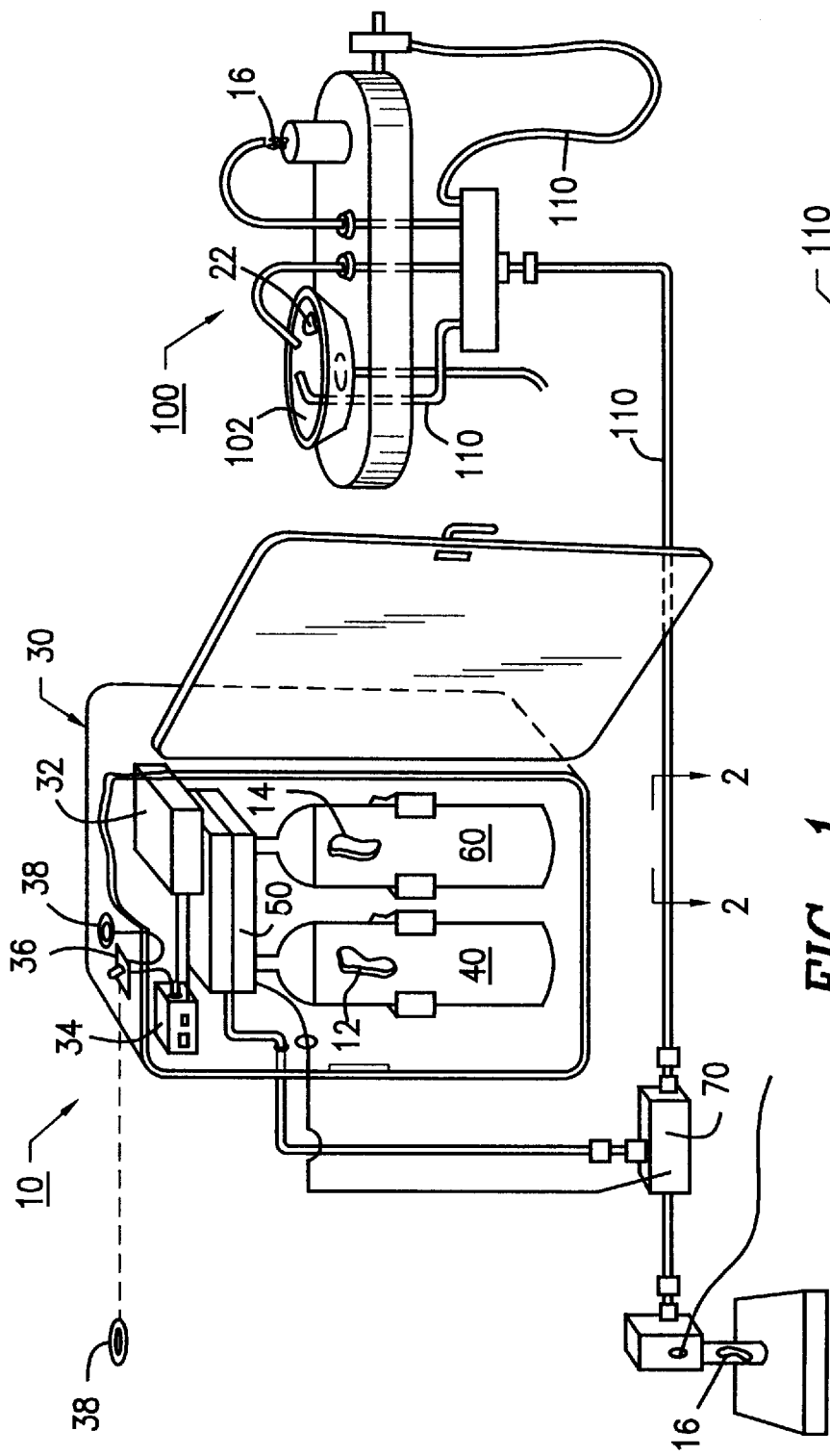
FIG. 1 is a front perspective view of an asepsis apparatus in operational use for supplying the disinfectant composition of the present invention showing the flow of the disinfectant composition through the asepsis apparatus to the dental water system and its water lines for the cleansing and sanitizing of its contaminated surfaces.

The asepsis disinfectant composition of the present invention includes agents in the following categories: an anti-infective and antiseptic agent, a water purifying agent, a cleansing agent, an anti-oxidant and stabilizer, a scrubbing agent, a pH adjuster and control agent, a diluent, and a gas propellant. In the preferred embodiment of the present invention, the asepsis disinfectant composition having cleansing and decontamination properties includes the following:

| CHEMICAL COMPONENT | LIQUID FORM % RANGE (BY WEIGHT) |
|---|---|
| I. An anti-infective, germicidal and antiseptic agent, such as hydrogen peroxide ($H_2O_2$), urea hydrogen peroxide or betaine hydrochloride. | 13.0% to 45.5% |
| II. A water purifying agent, such as iodine ($I_2$), iodine penta-fluoride ($IF_5$), iodine monobromide (IBr), iodine chloride (IC1), iodine halides, iodophors, and tetraglycine hydroperiodide. | 4.0% to 14.0% |
| III. A cleansing and surfactant agent, such as boric acid ($H_3BO_3$), meta boric acid ($H_3BO_2$), salts of boric acid, benzoic acid, bismuth with halogen, bismuth subnitrate, chlorhexidine, chlorhexidine gluconate, citric acid, hippuric acid, hydrochloric acid, kojic acid, lauric acid, sodium oleate, sodium potassium bicarbonate alkalizer or zinc sulfate. | 10.0% to 23.0% |
| IV. An anti-oxidant and stabilizer agent, such as lecithin, glycerides, choline, linoleic acid, linoleic diethanolamide or black walnut hull tincture (10%). | 4.0% to 8.0% |
| V. A scrubbing agent, such as zinc oxide solution, borax, calcium hydroxide, magnesium hydroxide, magnesium oxide, potassium carbonate, potassium oxide, selenium oxide or sodium bicarbonate. | 4.0% to 8.0% |
| VI. A pH adjuster and control agent, such as ascorbic acid, acetic acid, benzoic acid, citric acid, ethanolamine, fumaric acid, glycine, hippuric acid, hydroiodic acid, hydrochloric acid, kojic acid, nitric acid, phosphoric acid, sodium bicarbonate, sodium hydroxide or sulfuric acid. | Trace Amounts to 2.0% |
| VII. A sterile gas propellant, such as compressed air, carbon dioxide, nitrogen or helium. | 2.0% to 6.0% |
| VIII. A diluent, such as pure water, ethanol, isopropanol, and polyvinyl alcohols. | 35.0% to 50.0% |

The anti-infective, germicidal and antiseptic agent of the asepsis disinfectant composition of the present invention is functionally defined to include chemical constituents that are bactericidal, virucidal, sporicidal, fungicidal and parasiticidal. The anti-infective and antiseptic agent of the disinfectant composition of the present invention is used for killing pathogenic and non-pathogenic organisms. Anti-infective and antiseptic agents (such as hydrogen peroxide, urea hydrogen peroxide and equivalents thereof) being used in this disinfectant composition are particularly effective against many aerobic and anaerobic gram positive and gram negative bacteria including but not limited to those of the genera Actinobacillus, Bacillus, Bacteroides, Campylobacter, Corynebacterium, Enterococcus, Escherichia, Klebsiella, Legionella, Mycobacterium, Neisseria, Salmonella, Staphloycoccus, Streptococcus, and Treponema; fungi including but not limited to those of the genus Aspergillus, Blastomyces, Candida, Coccidioides, Fusarium, Mucoraceae, Paracoccidiodes, and Sporothrix; parasites including but not limited to those of the genus Chlamydia, Endomeba, Leishmania, Naegleria, Nippostrongycus, Plasmodium, Pneumocystis, Schistosoma, Tepanosoma, Toxoplasma, and Trichomonas; and viruses including but not limited to those of the genus classifications Cytomegalovirus, Human immunodeficiency virus, Hydrophilic viruses, Lipophilic viruses, Lymphocytic viruses, and Tacaribe virus. The anti-infective and antiseptic agent for destroying pathogenic and non-pathogenic organisms, as previously described above, includes chemical agents selected from the group consisting of hydrogen peroxide, urea hydrogen peroxide, and betaine-hydrochloride. Hydrogen peroxide ($H_2O_2$) is the primary anti-infective and antiseptic agent used in the formulation of the disinfectant composition of the present invention. Hydrogen peroxide ($H_2O_2$) works as a germicide by releasing oxygen gas ($O_2$) within the water system and its water lines, such that the free oxygen radial ($O^-$) is reactive to organisms and it disrupts the cell wall of microorganisms, effectively killing them. Temperature, pH, concentration of the hydrogen peroxide ($H_2O_2$), and the number of organisms are important factors which influence the germicidal effect of the hydrogen peroxide ($H_2O_2$) solution. Hydrogen peroxide is environmentally safe, non-accumulative, non-toxic and non-corrosive when disposing of it through a sewerage treatment plant, as it breaks down into water ($H_2O$) and oxygen ($O_2$) over time. The concentration of hydrogen peroxide ($H_2O_2$) used in this formulation of disinfectant solution is in the range of a 30% solution to a 41% solution, and as such the concentration used in this formulation will not harm, burn or irritate human soft tissue. The anti-infective and anti-septic agent is at least 13.0% by weight of the disinfectant composition and has an overall range of 13.0% to 45.5% by weight of the disinfectant composition.

Figure 3:
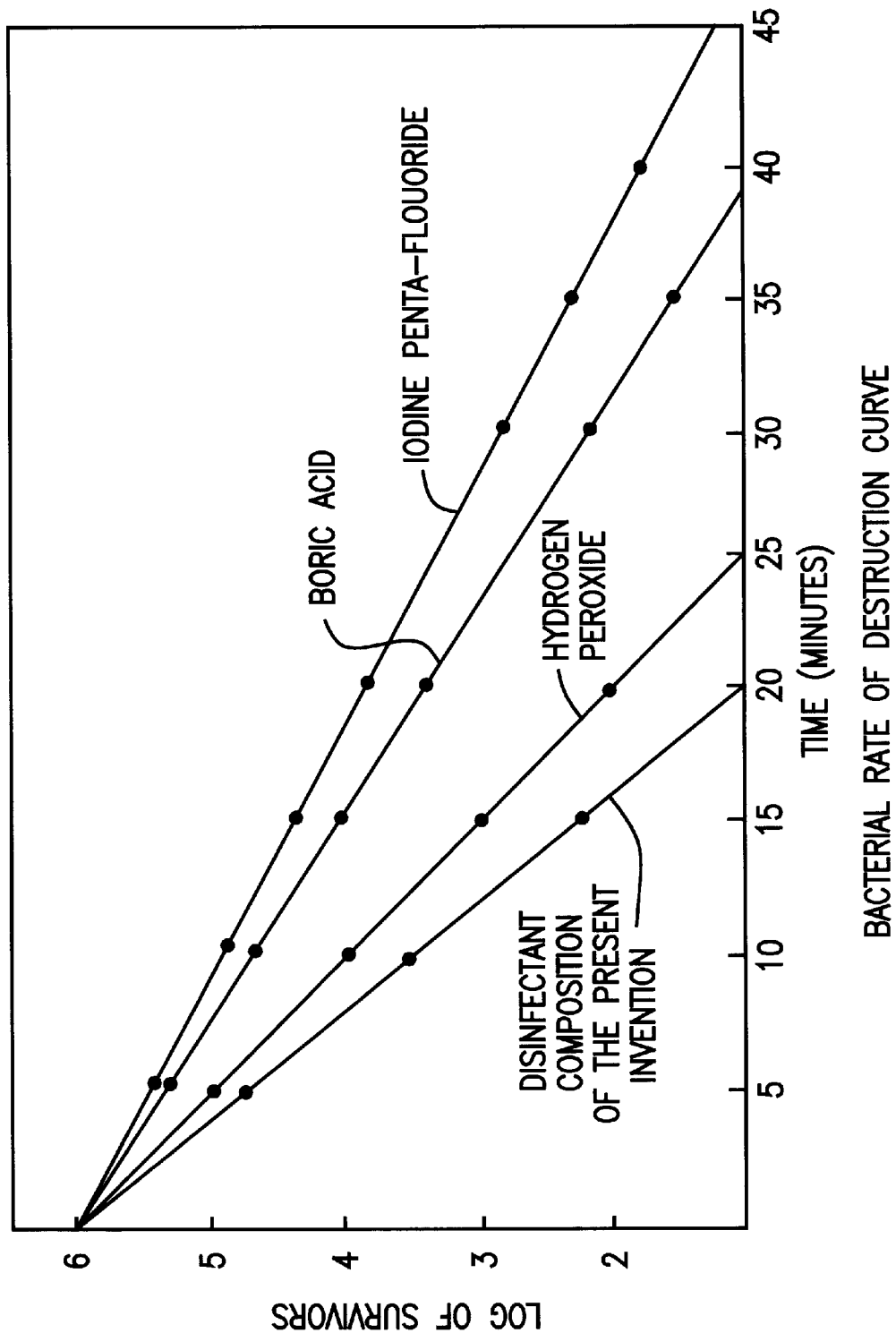
FIG. 3 is a graph showing the bacterial time rate of destruction curve for the operational use of the disinfectant composition of the present invention.

In addition, when hydrogen peroxide ($H_2O_2$) and boric acid ($H_3BO_3$) are mixed together in a solution, as they are in the formulation of the disinfectant composition of the present invention, the germicidal properties of each constituent are synergistically enhanced, as shown in FIG. 3 of the drawings.

The water purifying agent of the asepsis disinfectant composition of the present invention is functionally defined to include chemical constituents that are germicidal, as well as being a good detergent and sanitizer complex. The water purifying agent of the disinfectant composition of the present invention is used for killing pathogenic and non-pathogenic organisms. Water purifying agents (such as iodine, iodine penta-fluoride, iodine monobromide, iodine chloride, iodine-halides, idophors and tetraglycine hydroperiodide) being used in this disinfectant composition are particularly effective against many aerobic and anaerobic gram positive and gram negative bacteria including but not limited to those of the genera Acinetobacter, Actinobacillus, Bacillus, Bacteroides, Citrobacter, Clostridium, Corynebacterium, Enterobacter, Enterococcus, Escherichia, Haemophilus, Klebsiella, Kluyvra, Lactobacillus, Moraxella, Morganella, Mycobacterium, Mycoplasma, Neisseria, Propionibacterium, Proteus, Providencia, Pseudomonas, Salmonella, Serrata, Shigella, Staphylococcus, Streptococcus, Torulopsis, and Yersina; fungi including but not limited to those of the genus Aspergillus, Candida and Fusarium; parasites including but not limited to those of the genus Protozoa and Trichomonas; and viruses including but not limited to those of the genus classifications of Hydrophilic viruses, Lipophilic viruses and Vesicular stomatitis virus. The water purifying agent for destroying pathogenic and no-pathogenic organisms, as previously described above, includes chemical agents selected from the group consisting of iodine penta-fluoride ($IF_5$)

iodine monobromide (IBr), iodine ($I_2$), iodine chloride (ICl), iodine-halides, iodophors and tetraglycine hydroperiodide (iodine 50).

Iodine penta-fluoride ($IF_5$) is the preferred water purifying agent used in the formulation of the disinfectant composition of the present invention. Iodine penta-fluoride ($IF_5$) works as a microbicide because of its strong oxidative property, as well as the direct combination of the free iodine radical ($I^-$) with the cell proteins of the microorganism, which effectively destroys the cell protein, thus killing the microorganism. The microbicidal effectiveness of iodine-halides and iodophors (iodine complexes) decreases greatly with an increase in pH. For maximum activity, solutions should be used having a pH of 5.0 or lower. Activity is relatively slow at a pH 7.0. This is of practical importance for in-use dilution where the concentration of iodine is low, since the diluent water used may cause an increase in pH sufficient to reduce materially the effectiveness of the iodine-halide or iodophor being used. Iodine penta-fluoride ($IF_5$) is stable, dissolves readily in water and alcohol and has a negligible odor. Iodine penta-fluoride ($IF_5$) is a water purifying chemical when added to contaminated water, and turns the contaminated water into potable drinking water; and is most commonly used by military personnel in the field to sterilize small drinking water supplies. Iodine penta-fluoride ($IF_5$) is preferred over chlorine halide compounds for water disinfection because its use does not result in objectionable tastes and odors. Further, chlorine halide and chlorine compounds are corrosive to metals within dental air, water and vacuum systems and their respective air, water and vacuum lines. The concentration of the iodine penta-f luoride ($IF_5$) used in this formulation of disinfectant solution is in the range of a 3% solution to a 10% solution, and as such the concentration used in this formulation will not harm or irritate human physiology. The water purifying agent is at least 4.0% by weight of the disinfectant composition, and has an overall range of 4.0% to 14.0% by weight of the disinfectant composition.

The cleansing agent of the asepsis disinfectant composition of the present invention is functionally defined to include chemical constituents that are surfactants and astringents, as well as bactericidal, virucidal and fungicidal. The cleansing agent of the disinfectant composition of the present invention is used for killing pathogenic and non-pathogenic organisms and for removing biofilm, organic scum, bacterial plaques from surfaces. Cleansing agents (such as boric acid, citric acid, chlorhexidine, chlorhexidine gluconate and equivalents thereof) being used in this disinfectant composition are particularly effective against many aerobic and anaerobic gram positive and gram negative bacteria and viruses including but not limited to those of the genera Acinetobacter, Aeromonas, Bacillus, Campytobacter, Citrobacter, Corynebacterium, Enterobacter, Enterococcus, Escherichia, Haemophilus, Klebsiella, Listeria, Moraxella, Morganella, Mycobacterium, Neisseria, Pasteurella, Propionibacterium, Proteus, Providencia, Pseudomonas, Salmonella, Serrata, Shigella, Staphylococcus, Streptococcus, Vibrio, Xanthomonas and Yersinia; and fungi including but not limited to those of the genus Aspergillus, Candida, and Fusarium. The cleansing agent for destroying pathogenic and non-pathogenic organisms, as previously described above, includes chemical agents selected from the group consisting of boric acid ($H_3BO_3$), meta boric acid ($H_3BO_2$), salts of boric acid, benzoic acid, bismuth with halogen, bismuth subnitrate, chlorhexidine, chlorhexidine gluconate, citric acid, hippuric acid, kojic acid, lauric acid, sodium oleate, sodium potassium bicarbonate alkalizer and zinc sulfate.

Boric acid ($H_3BO_3$) is the preferred cleansing agent used in the formulation of the disinfectant composition of the present invention. Boric acid ($H_3BO_3$) works as an astringent because of its strong detergent, bleaching and surfactant properties, as boric acid is derived from borax, a naturally occurring mineral. Boric acid is a potent cleansing agent in the preferred formulation of the disinfectant composition, as it removes biofilm (plaque) from internal and external surfaces of medical and dental equipment. In addition, boric acid ($H_3BO_3$) works as a bactericide and fungicide by injuring the cell membrane within the microorganism, as well as causing the decarboxylation of amino acids in the cell structure, which effectively destroys the cell structure, cell membrane and cell protein, thus killing the microorganism. Boric acid is also used as an optical rinse for eye infections, mouth wash and other topical applications, as it is a known antiseptic and anti-infective in the medical and cosmetic industries. Boric acid is safe to use on humans and is non-toxic to the environment. Boric acid has no deleterious effects on the metal, plastic and ceramic components use in medical and dental equipment. Further, when boric acid ($H_3BO_3$) is combined with zinc oxide (ZnO) in the disinfectant solution of the preferred formulation, as shown in the table of Formulation No. 1, this combination becomes an even greater surfactant as compared to the additive effects of each chemical constituent by itself. Boric acid also increases the germicidal and water purifying property of iodine. It also stabilizes iodine and increases shelf life. Zinc oxide also is a virucide as well as a scrubbing agent. The cleansing agent is at least 10.0% by weight of the disinfectant composition, and has an overall range of 10.0% to 23.0% by weight of the disinfectant composition.

The anti-oxidant and stabilizer agent of the asepsis disinfectant composition of the present invention is functionally defined to include chemical constituents that are anti-oxidants, stabilizers, emulsifiers and act as a carrier agent for substances which are insoluble in water but which require dilution. The anti-oxidant and stabilizer agent, as described in the above, includes chemical agents selected from the group consisting of lecithin, glycerides, choline, linoleic diethanolamide, linoleic acid and black walnut hull tincture (10%).

Lecithin is the preferred anti-oxidant stabilizer agent used in the formulation of the disinfectant composition of the present invention. Lecithin works as a stabilizer in the preferred formulation, such that the lecithin stabilizes the hydrogen peroxide ($H_2O_2$) in the presence of boric acid ($H_3BO_3$) and iodine penta-fluoride ($IF_5$) so that the hydrogen peroxide ($H_2O_2$) does not release its free oxygen ($O^-$) too readily or breakdown quickly to free hydrogen ($H_2$) and free oxygen ($O_2$). Thus, the addition of lecithin to the formulation of the disinfectant composition prolongs the effectiveness and potency of the hydrogen peroxide ($H_2O_2$) as a germicide. Lecithin is a naturally occurring lipid material and is commonly recognized as a food supplement being safe for human ingestion. Lecithin is often used as an emulsifier and stabilizer agent in the food and cosmetic industries. The anti-oxidant and stabilizer agent is at least 4.0% by weight of the disinfectant composition, and has an overall range of 4.0% to 8.0% by weight of the disinfectant composition.

The scrubbing agent of the asepsis disinfectant composition of the present invention is functionally defined to include chemical constituents that are abrasives and cleansers. The scrubbing agent, as described in the above, includes chemical agents selected from the group consisting of zinc oxide (ZnO), borax selenium oxide, calcium bicarbonate, calcium hydroxide, magnesium hydroxide, magnesium oxide, potassium oxide, sodium bicarbonate and sodium potassium bicarbonate alkalizer. Zinc oxide (ZnO) is the preferred scrubbing agent used in the formulation of the disinfectant composition of the present invention. Zinc oxide is used in medicaments, dental cements and skin protectants, as it is safe to use on humans and is non-toxic to the environment. As a scrubbing agent, zinc oxide (ZnO) is introduced into the preferred formulation, as shown in the table of Formulation No. 1, as a colloidal suspension in a 20% zinc oxide solution. The colloidal suspension keeps the zinc oxide (ZnO) in suspension and prevents it from settling out and clogging any of the internal components within the dental and medical equipment being cleaned. Zinc oxide (ZnO) is non-reactive to metals and plastics and will not plate the valves, tubing and component parts of dental water systems. The presence of zinc oxide (ZnO) in the preferred formulation of the disinfectant composition renders the boric acid ($H_3BO_3$) a more effective surfactant, as previously mentioned. The scrubbing agent is at least 4.0% by weight of the disinfectant composition, and has an overall range of 4.0% to 8.0% by weight of the disinfectant composition. The preferred weight % of zinc oxide (ZnO) is 4.5% of the total disinfectant composition.

The pH adjuster and control agent of the asepsis disinfectant composition of the present invention is functionally defined to include chemical constituents that are acidulents, alkalinizers, buffers and/or neutralizers. The pH adjusters and control agents for the disinfectant composition of the present invention are used for buffering, neutralizing, or acidifying the disinfectant composition from a basic (an alkaline) condition or neutral condition to a slightly acidic condition having a pH in the range of 5.0 to 6.9 with a preferred pH of 5.5. The pH adjusters and control agents for acidifying the disinfectant composition are selected from the group consisting of sodium hydroxide (NaOH), sodium bicarbonate ($NaHCO_2$), glycine, acetic acid, ascorbic acid, benzoic acid, citric acid, fumaric acid, hippuric acid, hydrochloric acid, hydriodic acid, kojic acid, nitric acid, phosphoric acid, sulfuric acid, ethanolamine, equivalents and combinations thereof, being in the overall range of trace amounts to 2.0% by weight of the disinfectant composition.

The sterile gas propellant of the asepsis disinfectant composition of the present invention is functionally defined to include chemical constituents that are non-reactive carrier gases for pressurization of canisters for use as an aerosol spray disinfectant. The gas propellant for the disinfectant composition of the present invention is used to spray the disinfectant solution under pressure from the aerosol canisters 20 and 30 via the asepsis apparatus 10 as shown in FIG. 1 of the drawings in order to decontaminate the water system and lines at a dental facility. The gas propellants being used as a carrier gas for the disinfectant composition are selected from the group consisting of sterile gases such as compressed air ($O_2/N_2$), carbon dioxide ($CO_2$), nitrogen ($N_2$), helium (He) and equivalents thereof. The gas propellant is at least 2.0% by weight of the disinfectant composition, and has an overall range of 2.0% to 6.0% by weight of the disinfectant composition. The preferred weight % of the gas propellant is 2.0% of the total disinfectant composition.

The diluent of the asepsis disinfectant composition of the present invention is functionally defined to include chemical constituents that are carriers having the capability to dissolve the various and aforementioned chemical agents used in the formulations of the present invention. Additionally, as shown in Formulation No. 4, the carrier may also act as a germicide (i.e. alcohols), and act as a substitute purifying agent in place of the iodine-halide complex as shown by Formulation No. 1 of the preferred embodiment. Alcohols are also used for killing pathogenic and non-pathogenic microorganisms and work as a germicide because the alcohol acts as a coagulant and denaturalizer of cell proteins of the microorganism, which effectively destroys the cell protein membrane (wall), thus killing the microorganism. Biocide agents (such as ethanol, 2-propanol, polyvinyl alcohol and equivalents thereof) being used in the alternate formulations of the disinfectant composition are particularly effective against many aerobic and anaerobic gram positive and gram negative bacteria including but not limited to those of the genera Acinetobacter, Aeromonas, Bacillus, Campytobacter, Citrobacter, Corynebacterium, Enterobacter, Enterococcus, Escherichia, Haemophilus, Klebsiella, Listeria, Microsporum, Moraxella, Morganella, Mycobacterium, Neisseria, Pasteurella, Propionibacterium, Proteus, Providencia, Pseudomonas, Salmonella, Serrata, Shigella, Staphylococcus, Streptococcus, Trichophyton, Vibrio, Xanthomonas and Yersinia; and fungi including but not limited to those of the genus Aspergillus, Candida, and Fusarium; viruses including but not limited to those of the genus classifications of Adenovirus-type 2, Coxsackie B-1 virus, Echovirus-type 6, Foot and mouth disease virus, Fowl pox virus, Hepatitis-B virus, Herpes simplex virus, Human immunodeficiency virus, Influenza Asian virus, Newcastle virus, Poliovirus-type 1, Rotavirus, vaccinia virus; and parasites including but not limited to those of the genus Chlamydia, Schistosoma, and Trichomonas. The diluent, as described above, include chemical constituents selected from the group consisting of water ($H_2O$), ethanol/ethyl alcohol ($CH_3CH_2OH$), isopropyl alcohol ($CH_3CHOHCH_3$) and polyvinyl alcohol. Water ($H_2O$) is the preferred diluent used in the formulation of the disinfectant composition of the present invention. Water ($H_2O$) works well as a carrier because of its ability to dilute and put into solution all of the chemical compounds associated with the preferred formulation, as shown in the table of Formulation No. 1. As a substitute for water ($H_2O$), alcohols such as ethanol, isopropanol and polyvinyl alcohol also work well as a carrier because of their ability to dilute and put into solution all of the chemical compounds associated with the alternate formulation, as shown in the tables of Formulations No. 2, No. 3 and No. 4. Also, alcohols act as a germicide, as previously described. The diluent is at least 35.0% by weight of the disinfectant composition, and has an overall range of 35.0% to 50.0% by weight of the disinfectant composition.

The following numbered formulation examples illustrate the preferred embodiment and alternate embodiments of representative disinfectant composition formulations embodying the present invention in using the aforementioned chemical constituents and appropriate substitutes within the disinfectant composition.

FORMULATION NO. 1
ASEPSIS DISINFECTANT COMPOSITION
PREFERRED EMBODIMENT

| INGREDIENT CATEGORIES | CHEMICAL COMPOUND | PERCENT CONCENTRATION OF SOLUTION | WEIGHT IN OUNCES | PERCENT BY WEIGHT |
|---|---|---|---|---|
| I. ANTI-INFECTIVE & ANTISEPTIC AGENT | HYDROGEN PEROXIDE ($H_2O_2$) | 30.0% | 5.0 oz. | 22.7% |
| II. WATER PURIFYING AGENT | IODINE FLUORIDE ($IF_5$) | 5.0% | 1.0 oz. | 4.5% |
| III. CLEANSING AGENT | BORIC ACID ($H_3BO_3$) | 100.0% | 5.0 oz. | 22.7% |
| IV. ANTI-OXIDANT & STABILIZER AGENT | LECITHIN | SOLID | 1.0 oz. | 4.5% |
| V. SCRUBBING AGENT | ZINC OXIDE (ZnO) | 20.0% | 1.0 oz. | 4.5% |
| VI. pH ADJUSTER & CONTROL AGENT | CITRIC ACID | SOLID | 0.2 oz. | 1.0% |
| VII. GAS PROPELLANT | COMPRESSED AIR ($O_2/N_2$) | GAS | 0.4 oz. | 2.0% |
| VIII. DILUENT | WATER ($H_2O$) | 100.00 | 8.4 oz. | 38.1% |
|  | TOTALS | — | 22.0 oz. | 100.0% |

FORMULATION NO. 2
ASEPSIS DISINFECTANT COMPOSITION
AN ALTERNATE EMBODIMENT

| INGREDIENT CATEGORIES | CHEMICAL COMPOUND | PERCENT CONCENTRATION OF SOLUTION | WEIGHT IN OUNCES | PERCENT BY WEIGHT |
|---|---|---|---|---|
| I. ANTI-INFECTIVE & ANTISEPTIC AGENT | HYDROGEN PEROXIDE ($H_2O_2$) | 41.0% | 3.0 oz. | 13.6% |
| II. WATER PURIFYING AGENT | IODOPHOR | 10.0% | 3.0 oz. | 13.6% |
| III. CLEANSING AGENT | BORIC ACID ($H_3BO_3$) | 100.0% | 3.0 oz. | 13.6% |
| IV. ANTI-OXIDANT & STABILIZER AGENT | LECITHIN | SOLID | 1.0 oz. | 4.5% |
| V. SCRUBBING AGENT | ZINC OXIDE (ZnO) | 20.0% | 1.0 oz. | 4.5% |
| VI. pH ADJUSTER & CONTROL AGENT | FUMARIC ACID | SOLID | 0.2 oz. | 1.0% |
| VII. GAS PROPELLANT | CARBON DIOXIDE ($CO_2$) | GAS | 0.8 oz. | 3.6% |
| VIII. DILUENT | ETHANOL ($CH_3CH_2OH$) | 100.00 | 10.0 oz. | 45.6% |
|  | TOTALS | — | 22.0 oz. | 100.0% |

FORMULATION NO. 3
ASEPSIS DISINFECTANT COMPOSITION
AN ALTERNATE EMBODIMENT

| INGREDIENT CATEGORIES | CHEMICAL COMPOUND | PERCENT CONCENTRATION OF SOLUTION | WEIGHT IN OUNCES | PERCENT BY WEIGHT |
|---|---|---|---|---|
| I. ANTI-INFECTIVE & ANTISEPTIC AGENT | UREA HYDROGEN PEROXIDE | 35.0% | 4.0 oz. | 18.2% |
| II. WATER PURIFYING AGENT | IODINE MONO-BROMIDE (IBR) | 5.0% | 1.0 oz. | 4.5% |
| III. CLEANSING AGENT | CHLORHEXIDINE | 100.0% | 3.0 oz. | 13.6% |
| IV. ANTI-OXIDANT & STABILIZER AGENT | LECITHIN | SOLID | 1.0 oz. | 4.5% |
| V. SCRUBBING AGENT | ZINC OXIDE (ZnO) | 20.0% | 1.0 oz. | 4.5% |
| VI. pH ADJUSTER & CONTROL AGENT | ETHANOLAMINE ($NH_2CH_2CH_2OH$) | SOLID | 0.5 oz. | 2.3% |
| VII. GAS PROPELLANT | NITROGEN ($N_2$) | GAS | 0.5 oz. | 2.3% |
| VIII. DILUENT | ISOPROPYL ALCOHOL ($CH_3CHOHCH_3$) | 100.00 | 11.0 oz. | 49.9% |
| | TOTALS | — | 22.0 oz. | 100.0% |

FORMULATION NO. 4
ASEPSIS DISINFECTANT COMPOSITION
AN ALTERNATE EMBODIMENT

| INGREDIENT CATEGORIES | CHEMICAL COMPOUND | PERCENT CONCENTRATION OF SOLUTION | WEIGHT IN OUNCES | PERCENT BY WEIGHT |
|---|---|---|---|---|
| I. ANTI-INFECTIVE & ANTISEPTIC AGENT | HYDROGEN PEROXIDE ($H_2O_2$) | 41.0% | 5.0 oz. | 22.7% |
| II. WATER PURIFYING AGENT | NOT APPLICABLE | | | |
| III. CLEANSING AGENT | BORIC ACID ($H_3BO_3$) | 100.0% | 5.0 oz. | 22.7% |
| IV. ANTI-OXIDANT & STABILIZER AGENT | LECITHIN | SOLID | 1.0 oz. | 4.5% |
| V. SCRUBBING AGENT | BISMUTH WITH HALOGEN | 20.0% | 1.0 oz. | 4.5% |
| VI. pH ADJUSTER & CONTROL AGENT | FUMARIC ACID | SOLID | 0.2 oz. | 1.0% |
| VII. GAS PROPELLANT | CARBON ($CO_2$) | GAS | 0.8 oz. | 3.6% |
| VIII. DILUENT | ETHANOL ($CH_3CH_2OH$) | 100.00 | 9.0 oz. | 41.0% |
| | TOTALS | — | 22.0 oz. | 100.0% |

OPERATION OF THE PRESENT INVENTION

The asepsis disinfectant composition of the present invention can be used for a variety of cleansing and sanitizing applications for the removal of biofilm and microorganisms from contaminated surfaces (internal and external) of equipment and their associated component parts and transfer lines (air, water and vacuum) in the dental, food, laundry and medical industries, as well as in the home/personal use market. The asepsis disinfectant composition in liquid form can be used in different modes of operational applications, such as in disinfectant handwipes, disinfectant towellettes, disinfectant hand-pump spray containers, disinfectant pressurized aerosol spray canisters, and bottles of liquid disinfectant solution for use in soaking or flushing applications of instruments and component parts in all of the aforementioned industrial, scientific, professional and consumer markets.

Figure 2:
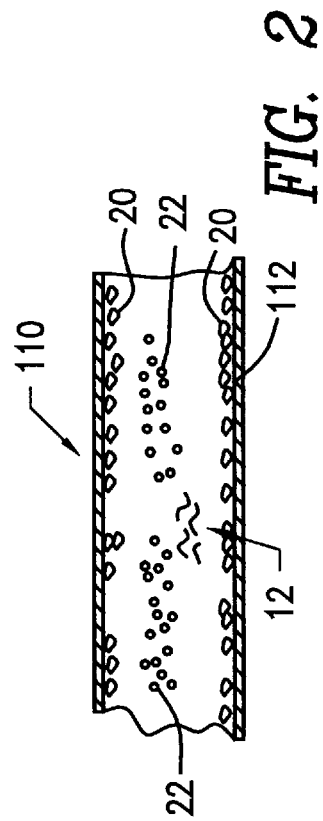
FIG. 2 is an enlarged cross-sectional view of the water inlet line to the dental water system taken along lines 2—2 of FIG. 1 showing the cleansing and sanitizing action of the disinfectant composition of the present invention for removing of the biofilm accumulation and sanitizing of the microbial contaminants from the interior surface of the water inlet line.

In particular, the disinfectant compositions of the present invention may be used in an asepsis dispenser apparatus 10, as shown in FIGS. 1 and 2 of the drawings, for the cleansing and decontamination of the biofilm and microbial contaminants within a water system 100 and water lines 110 used in medical and dental facilities (asepsis dispenser apparatus 10 is fully described in a copending patent application Serial No. 09/047,550, incorporated herein by reference). Asepsis apparatus 10 includes a pair of pressurized aerosol canisters 40 and 60 in which canister 40 contains one of the formulations of the disinfectant compositions 12 of the present invention, as shown in the tables of Formulation Nos. 1 through 4. Canister 60 contains only a flavored (peppermint, or spearmint), 30% hydrogen peroxide ($H_2O_2$) solution 14 which is used in conjunction with the disinfectant composition 12 in the daily cleansing and sanitizing procedure for microbial decontaminating and biofilm removal from the contaminated surfaces within the water systems 100 and their associated water lines 110 of the dental and medical units. Asepsis dispenser apparatus further includes a housing 30 having a power source 32, a programmable electronic cycle timer device 34, a daytime/nighttime switch 36, a start-up switch 38, a first three-way solenoid valve 50 therein and a second three-way solenoid valve 70 externally placed. The disinfectant composition 12 is intended to remain within the water system 10 and its water lines 110 for at least 8 hours, during non-working time (nighttime: i.e. 10 P.M. to 6 A.M.) at the dental or medical facility, such that the cleansing and sanitizing of the water system 100 and the water lines 110 by the disinfectant composition 12 is done once per day shortly after the dental water system 100 in shut-down for the day. In the morning the water system 100 is then flushed-out with fresh water 16 for a period of at least three (3) minutes in preparation of the new work day. The purging with fresh water 16 allows the disinfectant composition 12 to be fully flushed-out of the water system 100 and its waterlines 110, such that patients will not be bothered by any residual chemical tastes after the flushing.

There is a two-fold simultaneous operational mechanism that enables the disinfectant composition 12 of the present invention to function and act as a cleanser and sanitizer at the same time. The cleansing mechanism for the removal of biofilm 20, as shown in FIG. 2 of the drawings, from a soiled surface 112 of a water line 110 is achieved by physical abrasiveness, abradant and astringent properties, in some of the chemical constituents used in the formulations of the disinfectant composition. These cleansing chemical compounds include boric acid ($H_3BO_3$), zinc oxide (ZnO) and citric acid. The sanitizing mechanism for destroying and killing of pathogenic and non-pathogenic microorganisms 22 from a contaminated surface 102 of a water system 100 is achieved by multiple chemical reactions affecting the cell structure of the microbes 22 which are caused by some of the chemical constituents used in the formulations of the disinfectant composition. These germicidal chemical compounds include hydrogen peroxide ($H_2O_2$), boric acid ($H_3BO_3$), iodine penta-fluoride ($IF_5$), iodine monobromide (IBr), chlorhexidine, ethanol ($CH_3CH_2OH$) and isopropanol ($CH_3CHOHCH_3$). The chemical reactions affecting cell structure of microorganisms causing their death include the following (based on the formulations of the present invention):

1. Hydrogen peroxide provides a free oxygen radical ($O^-$) which is reactive to the cell structure of the microorganism and it disrupts the cell wall of the microorganism, effectively killing them.
2. Iodine penta-fluoride provides a strong oxidative mechanism such that the free iodine radical ($I^-$) reacts with cell protein of the cell wall of the microorganism, which effectively destroys the cell protein, thus killing the microorganism.
3. Boric acid provides a free hydrogen radical ($H^+$) which is also reactive to the cell structure of the microorganism, and it injures the cell membrane within the microorganism by causing the decarboxylation of amino acids in the cell structure, which effectively destroys the cell protein, cell membrane and cell structure, thus killing the microorganism.
4. Ethanol and isopropyl alcohol act as a coagulant and denaturalizer of cell proteins within the cell membrane of the microorganism, which effectively destroys the cell protein of the cell membrane (wall), thus killing the microorganism.

The combination of the aforementioned germicidal chemical compounds included within the various formulations of the disinfectant composition of the present invention have an enhanced chemical effect in the destruction and killing of those microorganisms that come in contact with the disinfectant solution by shortening the time rate as shown by the bacterial rate of destruction curve in FIG. 3 of the drawings, and expanding the effective range of temperature and/or pH, as compared to the bacterial rate destruction curve of the individual chemical ingredients of hydrogen peroxide, boric acid and iodine penta-fluoride of the preferred embodiment.

The preferred and alternate embodiments of the disinfectant composition of the present invention effectively kills such pathogenic and non-pathogenic microorganisms as shown in the following genus classifications.

| BACTERIA | |
| --- | --- |
| Acampylobacter jejuni | Mycobacterium leprae* |
| Acinetobacter anitratus | Mycobacterium tuberculosis** |
| Actinobacillus | Mycoplasma pneumonia |
| actinomycetemoconita | Nesisseria gonorrhea** |
| Aeromonas hydrophila | Nesisseria meningitidis** |
| Bacillum cereus | Pasteurella multocida |
| Bacillus cereus | Propionibacterium acnes |
| Bacillus subtilis | Proteus mirabilis |
| Bacteroides fragilis | Proteus vulgaris |
| Bacteroides pneumosintes | Providenica stuartii |
| Campytobacter jejuni | Pseudomonas aeruginosa* |
| Citrobacter freundii | Pseudomonas cepacia |
| Citrobacter tropicalis | Pseudomonas maltophilia |
| Clostridium perfringens | Salmonella enteritidis** |
| Clostridium lortetii | Salmonella typhi** |
| Clostridium sordellii | Salmonella typhimurium** |
| Corynebacterium cystitidis | Salmonella typhosa |
| Corynebacterium diptheriae | Serrata marcescens |
| Enterobacter aerogenes | Serrata odorifera |
| Enterobacter agglomerans | Serrata rubideae |
| Enterobacter cloacae | Shigella sonnei |
| Enterobacter sakazakii | Staphylococcus agalactrae |
| Enterococcus proteiformis | Staphylococcus albus |
| Escherichia coli** | Staphyldcoccus auerus** |
| Group B Streptococci** | Staphylococcus epidemidis |
| Haemophilus influenzae | Staphylococcus pneumonia** |
| Klebsiella oxytoca | Staphylococcus pyogenes |
| Klebsiella planticola | Staphylococcus saprophyticus, |
| Klebsiella pneumoniae | Streptococcus agalactiae |
| Kluyvera asorbata | Streptococcus beta-hemolytic** |
| Lactobacillus casei | Streptococcus pneumoniae** |
| Legionella pneumophila** | Streptococcus pyogenes |
| Listeria monocytogenes | Torulopsis glabrata |
| Microsporum audouini | Treponema pallidum |
| Microsporu canis | Trichophyton mentagrophytes |
| Moraxella osloensis | Trichophyton rubrum |
| Morganella morganii | Vibro parahaemolyticus |
| | Xanthomonos maltophilia |
| | Yersinia enterocolitica |

-continued

II. FUNGI

| | |
|---|---|
| Aspergillus fumigatus | Coccidioides immitis |
| Aspergillus niger | Fusarium solani |
| Blastomyces | Histoplasma capsulatum |
| Candida albicans | Mucoraceae |
| Candida kreusii | Paracoccidiodes |
| Candida parapsilosis | Sporothrix |
| Coccidioides | |

III. PARASITES

| | |
|---|---|
| Endomeba histolytica | Pneumocystis carinii |
| Chlamydia psittaci | Protozoa |
| Leishmania major | Schistosoma mansoni |
| Naegleria fowleri | Tepanosoma cruzi |
| Nippostrongycus brasiliensis | Toxoplasma gondii |
| | Trichomonas vaginalis |
| Plasmodium yoelii | |
| Plasmodium berghei | |

IV. VIRUSES

| | |
|---|---|
| Adenovirus-type 2 | Influenza asian virus** |
| Coxsackie B-1 virus | Lipophilic viruses |
| Cytomegalovirus | Lymphocytic choriomeningitis virus |
| Echovirus-type 6 | |
| Foot and mouth disease virus | Newcastle virus |
| | Poliovirus-type 1 |
| Fowl pox virus | Rotavirus |
| Hepatitis B virus | Tacaribe virus |
| Herpes simplex virus** | Vaccinia virus |
| Human Immunodeficiency Virus** | Vesicular stomatitis virus |
| Hydrophilic viruses | |

*Common municipal water bacteria that cause illness that are found in contaminated and septic water.
**Pathogens that are introduced artificially by patients.

A variety of formulations of the disinfectant composition of the present invention are readily available, as some of the chemical constituents can be varied in strength of concentration for a particular chemical solution (i.e. hydrogen peroxide is available from 3% solutions to 41% solutions), as well as a few alternate chemical constituents can be substituted for the preferred chemical compound (i.e. iodine penta-fluoride can be substituted and changed to iodine monobromide as a replacement to the preferred iodine penta-fluoride or the iodine penta-fluoride can be eliminated completely and ethanol can be used as a purifying agent and a diluent). The potency of the formulation largely depends on the water quality from its source (i.e. municipal water supply, well water, reservoir, lake water, etc.), contamination within the general plumbing infrastructure at the medical or dental facility, or the degree and level of microbial contamination within the medical or dental water supply system and its lines. Also, regional water qualities may influence the effectiveness of the preferred formulation of the disinfectant composition, wherein the more contaminated water, the disinfectant composition of the preferred formulation will become less effective in killing the microorganisms in that water source; and vice versa wherein with less contaminated water, the disinfectant composition of the preferred formulation will become more effective in killing the microorganisms in that regional water source. The same holds true for older medical/dental equipment versus newer medical/dental equipment. The older the medical/dental equipment the less effective the preferred formulation of the disinfectant composition will be because biofilm (plaque) has been able to accumulate over longer periods of time. Newer medical/dental equipment may require a less potent formulation and/or a shorter interval/duration of disinfectant chemical purging of the newer water system units (i.e. 4 hours versus 8 hours of purging by the disinfectant composition) before acceptable water quality in the medical/dental water systems is achieved. Thus, a variety of formulations of the disinfectant composition will be formulated for manufacture (i.e. standard, low potency, high potency, type of microorganisms to be killed, etc.). It will not be possible to ascertain the ideal formulation under all circumstances without testing the protocols of application for use in a specific medical/dental water system in order to verify if the protocols of application for use are effective for a particular formulation of disinfectant solution applied to that specific medical/dental water system in operation. The practitioner after testing will choose the most effective formulation of the disinfectant composition that are available from the manufacturer.

The regulatory requirements for the disinfectant composition of the present invention would be minimal. This disinfectant composition will set a standard in CDCP (Center for Disease Control & Prevention) and FDA clearance would be readily given because of the benign nature of the chemical formulations of the disinfectant compositions. OSHA requirements would be very negligible, as there are no caustic or inhalation problems associated with the disinfectant composition of the present invention, as well as no special handling requirements connected to the manufacturing and shipping of the disinfectant composition, as all of the chemical ingredients are non-toxic, non-irritating and safe to human physiology. In addition, there are no EPA, state and country environmental liabilities involved with the disinfectant composition of the present invention, as all of the chemical ingredients that will be introduced into a typical municipal sewerage treatment system are all biodegradable (some naturally occurring), non-toxic and non-accumulative.

ADVANTAGES OF THE PRESENT INVENTION

Accordingly, it is an advantage of the present invention that it provides for a disinfectant composition in solution form for cleansing and decontaminating of contaminated and soiled surfaces, and infectious air, water and vacuum lines in order to kill and/or inactivate viruses, bacteria, funguses, and parasites on contact.

Another advantage of the present invention is that it provides a disinfectant composition which disinfects, filter, scrubs, cleans and decontaminates water systems having air and water lines; medical and dental devices; air filters; surfaces made of metal, plastic and wood; furniture; floors; walls; tile grout and the like.

Another advantage of the present invention is that it provides a disinfectant composition comprising hydrogen peroxide, an iodine halide complex, boric acid, lecithin, and zinc oxide such that these compounds are readily soluble in water or alcohol, stable, and have germicidal and cleansing properties.

Another advantage of the present invention is that it provides a disinfectant composition that is non-harmful to humans, safe and non-irritating to the skin, lungs, eyes and mucous membranes and having no caustic or inhalation problems to humans; and can be used as a skin disinfectant for humans and animals. In addition, the disinfectant is safe, non-toxic, and non-binding to the dental components that the disinfectant comes in contact with, such that patients will not be bothered by residual chemical tastes.

Another advantage of the present invention is that it provides a disinfectant composition that is non-corrosive to medical grade metals that include aluminum, brass, and stainless steel; and is also non-absorptive into materials that include fabrics (will not stain), plastics, ceramics, and woods.

Another advantage of the present invention is that it provides a disinfectant composition that can be used as a soak (i.e. as in surface wipe mini-towels), as a flush in washing and rinsing of medical devices, or as an aerosol spray to disinfect and clean inner and outer surfaces of biofilm and microbial contaminants within air, water and vacuum systems and their respective air, water and vacuum lines.

Another advantage of the present invention is that it provides a disinfectant composition that is environmentally safe wherein all of the ingredients of the composition that are introduced into a waste sewerage system are naturally occurring, non-toxic, non-flammable, non-accumulative and are bio-degradable by organisms within the sewerage treatment cycle.

A further advantage of the present invention is that it provides a disinfectant composition that may be mass produced at a low material cost for ingredients in an automated and economical manner and being readily affordable by the practitioner.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. An asepsis disinfectant and biofilm removal composition in liquid form, having biofilm cleansing properties for removing biofilm from a surface in contact with water, comprising:
    a) an anti-infective, antiseptic, anti-biofilm and germicidal agent for killing pathogenic and non-pathogenic organisms includes hydrogen peroxide; being in the range of 13.0% to 45.5% by weight of the disinfectant composition;
    b) a water purifying agent for acting as a detergent, a sanitizer and a bactericide selected from the group consisting of an iodine solution, and iodophors; being in the range of 4.0% to 14.0% by weight of the disinfectant composition;
    c) a biofilm cleansing agent for acting as a surfactant, astringent and an abradant in the removal of biofilm from contaminated surfaces, and as a bactericide, fungicide and virucide selected from the group consisting of boric acid, salts of boric acid, citric acid, sodium bicarbonate, potassium bicarbonate and zinc sulfate; being in the range of 10.0% to 23.0% by weight of the disinfectant composition;
    d) an anti-oxidant and stabilizer agent for stabilizing said anti-infective and antiseptic agent in said liquid disinfectant composition selected from the group consisting of lecithin, glycerides, linoleic acid, and black walnut hull tincture being a 10% solution; being in the range of 4.0% to 8.0% by weight of the disinfectant composition;
    e) a scrubbing agent for acting as an abrasive and a cleanser for the removal of biofilm from contaminated surfaces selected from the group consisting of zinc oxide solution, borax, magnesium oxide, potassium carbonate, and sodium bicarbonate; being in the range of 4.0% to 16.0% by weight of the disinfectant composition;
    f) at least one pH adjuster for acidifying said disinfectant composition from a basic or neutral condition to a slightly acidic condition having a pH in the range of 5.0 to 6.9; said pH adjuster selected from the group consisting of sodium bicarbonate, glycine, ascorbic acid, and citric acid; being in the range of trace amounts to 12.0% by weight of the disinfectant composition; and
    g) a diluent for diluting and dissolving into solution said anti-oxidant and stabilizer agent, said scrubbing agent, and said pH adjuster and control agent; said diluent includes water; being in the range of 35.0% to 50.0% by weight of the disinfectant composition.

2. An asepsis disinfectant composition in accordance with claim 1, further including a sterile gas propellant for acting as a non-reactive carrier gas for pressurization of canisters for use as an aerosol spray disinfectant.

3. An asepsis disinfectant composition in accordance with claim 2, wherein said sterile gas propellant is selected from the group consisting of compressed air, carbon dioxide, nitrogen and helium; being in the range of 2.0% to 6.0% by weight of said disinfectant composition.

4. An asepsis disinfectant composition in accordance with claim 1, wherein said anti-infective, antiseptic and germicidal agent is hydrogen peroxide and is 22.7% by weight of said disinfectant composition.

5. An asepsis disinfectant composition in accordance with claim 1, wherein said hydrogen peroxide is in the range of 30.0% to 41.0% concentration of the hydrogen peroxide solution for imparting a specific level of potency to said disinfectant composition.

6. An asepsis disinfectant composition in accordance with claim 1, wherein said water purifying agent is iodine pentafluoride solution and is 4.5% by weight of said disinfectant composition.

7. An asepsis disinfectant composition in accordance with claim 1, wherein said iodine pentafluoride solution has a 5.0% concentration by weight of iodine pentafluoride.

8. An asepsis disinfectant composition in accordance with claim 1, wherein said cleansing agent is boric acid and is 22.7% by weight of said disinfectant composition.

9. An asepsis disinfectant composition in accordance with claim 1, wherein said anti-oxidant and stabilizer agent is lecithin and is 4.5% by weight of said disinfectant composition.

10. An asepsis disinfectant composition in accordance with claim 1, wherein said scrubbing agent is a zinc oxide solution and is 4.5% by weight of said disinfectant composition.

11. An asepsis disinfectant composition in accordance with claim 1, wherein said zinc oxide solution has a 20.0% concentration by weight of zinc oxide.

12. An asepsis disinfectant composition in accordance with claim 1, wherein said diluent is pure water and is 38.1% by weight of said disinfectant composition.

13. An asepsis disinfectant and biofilm removal composition in liquid form, having germicidal and biofilm cleansing properties for removing biofilm from a surface in contact with water, comprising:
    a) an anti-infective, antiseptic and, anti-biofilm germicidal agent for killing pathogenic and non-pathogenic organisms includes hydrogen peroxide; being in the range of 13.0% to 45.5% by weight of the disinfectant composition;
    b) a biofilm cleansing agent for acting as an surfactant, astringent and an abradant in the removal of biofilm from contaminated surfaces, and as a bactericide, fungicide and virucide selected from the group consisting of boric acid, salts of boric acid, citric acid, sodium bicarbonate, potassium bicarbonate and zinc sulfate;

being in the range of 10.0% to 23.0% by weight of the disinfectant composition;

c) an anti-oxidant and stabilizer agent for stabilizing said anti-infective and antiseptic agent in said liquid disinfectant composition selected from the group consisting of lecithin, glycerides, linoleic acid, and black walnut hull tincture being a 10% solution; being in the range of 4.0% to 8.0% by weight of the disinfectant composition;

d) a scrubbing agent for acting as an abrasive and a cleanser for the removal of biofilm from contaminated surfaces selected from the group consisting of zinc oxide solution, magnesium oxide, sodium bicarbonate, calcium bicarbonate, borax, and potassium bicarbonate; being in the range of 4.0% to 16.0% by weight of the disinfectant composition;

e) at least one pH adjuster for acidifying said disinfectant composition from a basic or neutral condition to a slightly acidic condition having a pH in the range of 5.0 to 6.9; said pH adjuster selected from the group consisting of sodium bicarbonate, glycine, ascorbic acid, and citric acid; being in the range of trace amounts to 12.0% by weight of the disinfectant composition; and f) a diluent for diluting and dissolving into solution said anti-oxidant and stabilizer agent, said scrubbing agent, and said pH adjuster and control agent; said diluent includes water; being in the range of 35.0% to 50.0% by weight of the disinfectant composition.

14. An asepsis disinfectant composition in accordance with claim 13, further including a sterile gas propellant for acting as a non-reactive carrier gas for pressurization of canisters for use as an aerosol spray disinfectant.

15. An asepsis disinfectant composition in accordance with claim 14, wherein said sterile gas propellant is selected from the group consisting of compressed air, carbon dioxide, nitrogen and helium; being in the range of 2.0% to 6.0% by weight of said disinfectant composition.

16. An asepsis disinfectant composition in accordance with claim 12, wherein said anti-infective, antiseptic and germicidal agent is hydrogen peroxide and is 22.7% by weight of said disinfectant composition.

17. An asepsis disinfectant composition in accordance with claim 13, wherein said hydrogen peroxide is in the range of 30.0% to 41.0% concentration of the hydrogen peroxide solution for imparting a specific level of potency to said disinfectant composition.

18. An asepsis disinfectant composition in accordance with claim 13, wherein said cleansing agent is boric acid and is 22.7% by weight of said disinfectant composition.

19. An asepsis disinfectant composition in accordance with claim 12, wherein said anti-oxidant and stabilizer agent is lecithin and is 4.5% by weight of said disinfectant composition.

20. An asepsis disinfectant composition in accordance with claim 13, wherein said scrubbing agent is a zinc oxide solution and is 4.5% by weight of said disinfectant composition.

21. An asepsis disinfectant composition in accordance with claim 13, wherein said zinc oxide solution has a 20.0% concentration by weight of zinc oxide.

22. An asepsis disinfectant composition in accordance with claim 13, wherein said diluent is water and is 38.1% by weight of said disinfectant composition.

23. An asepsis disinfectant composition in liquid form, having germicidal and biofilm cleansing properties, comprising:

a) an anti-infective, antiseptic and germicidal agent for killing pathogenic and non-pathogenic organisms being hydrogen peroxide in the range of 13.0% to 45.5% by weight of the disinfectant composition;

b) a water purifying agent for acting as a detergent, a sanitizer and a bactericide being iodine penta-fluoride in the range of 4.0% to 14.0% by weight of the disinfectant composition;

c) a cleansing agent for acting as a surfactant, astringent and an abradant in the removal of biofilm from contaminated surfaces, and as a bactericide, fungicide and virucide being boric acid in the range of 10.0% to 23.0% by weight of the disinfectant composition;

d) an anti-oxidant and stabilizer agent for stabilizing said anti-infective and antiseptic agent in said liquid disinfectant composition being lecithin in the range of 4.0% to 8.0% by weight of the disinfectant composition;

e) a scrubbing agent for acting as an abrasive and a cleanser for the removal of biofilm from contaminated surfaces being zinc oxide in the range of 4.0% to 8.0% by weight of the disinfectant composition;

f) at least one pH adjuster for acidifying said disinfectant composition from a basic or neutral condition to a slightly acidic condition having a pH in the range of 5.0 to 6.9; said pH adjuster selected from the group consisting of sodium bicarbonate, acetic acid, citric acid, and ethanolamine; being in the range of trace amounts to 2.0% by weight of the disinfectant composition; and g) a diluent for diluting and dissolving into solution said anti-oxidant and stabilizer agent, said scrubbing agent, and said pH adjuster and control agent; said diluent being water in the range of 35.0% to 50.0% by weight of the disinfectant composition.

24. An asepsis disinfectant composition in accordance with claim 1, wherein said anti-infective, antiseptic, anti-biofilm and germicidal agent further includes urea hydrogen peroxide and betaine-hydrochloride; being in the range of 13.0% to 45.5% by weight of the disinfectant composition.

25. An asepsis disinfectant composition in accordance with claim 1, wherein said biofilm cleaning agent further includes bismuth subnitrate; being in the range of 10.0% to 23.0% by weight of the disinfectant composition.

26. An asepsis disinfectant composition in accordance with claim 1, wherein said anti-oxidant and stabilizer agent further includes choline; being in the range of 4.0% to 8.0% by weight of the disinfectant composition.

27. An asepsis disinfectant composition in accordance with claim 1, wherein said scrubbing agent further includes potassium iodide and selenium oxide; being in the range of 4.0% to 16.0% by weight of the disinfectant composition.

28. An asepsis disinfectant composition in accordance with claim 1, wherein said at least one pH adjuster further includes acetic acid, benzoic acid, phosphoric acid and ethanolamine; being in the range of trace amounts to 12.0% by weight of the disinfectant composition.

29. An asepsis disinfectant composition in accordance with claim 1, wherein said diluent further includes ethanol, isopropyl alcohol, isopropanol and polyvinyl alcohol; being in the range of 35.0% to 50.0% by weight of the disinfectant composition.

30. An asepsis disinfectant composition in accordance with claim 13, wherein said anti-infective, antiseptic, anti-biofilm and germicidal agent further includes urea hydrogen peroxide and betaine-hydrochloride; being in the range of 13.0% to 45.5% by weight of the disinfectant composition.

31. An asepsis disinfectant composition in accordance with claim 13, wherein said biofilm cleaning agent further includes bismuth subnitrate; being in the range of 10.0% to 23.0% by weight of the disinfectant composition.

32. An asepsis disinfectant composition in accordance with claim 13, wherein said anti-oxidant and stabilizer agent further includes choline; being in the range of 4.0% to 8.0% by weight of the disinfectant composition.

33. An asepsis disinfectant composition in accordance with claim 13, wherein said scrubbing agent further includes potassium iodide and selenium oxide; being in the range of 4.0% to 16.0% by weight of the disinfectant composition.

34. An asepsis disinfectant composition in accordance with claim 13, wherein said at least one pH adjuster further includes acetic acid, benzoic acid, phosphoric acid and ethanolamine; being in the range of trace amounts to 12.0% by weight of the disinfectant composition.

35. An asepsis disinfectant composition in accordance with claim 13, wherein said diluent further includes ethanol, isopropyl alcohol, isopropanol and polyvinyl alcohol; being in the range of 35.0% to 50.0% by weight of the disinfectant composition.

* * * * *